United States Patent [19]

Wu et al.

[11] Patent Number: 5,075,317

[45] Date of Patent: Dec. 24, 1991

[54] SPIROFURANE DERIVATIVES

[75] Inventors: Edwin S. Wu; Ronald C. Griffith, both of Rochester, N.Y.

[73] Assignee: Fisons Corporation, Rochester, N.Y.

[21] Appl. No.: 369,324

[22] Filed: Jun. 21, 1989

[51] Int. Cl.$^5$ .................. A61K 31/435; C07D 491/07
[52] U.S. Cl. ...................................... 514/278; 546/16
[58] Field of Search ........................... 546/16; 514/278

[56] References Cited

U.S. PATENT DOCUMENTS 4,735,944  4/1988  Bolliger ................................ 546/17
4,940,295  7/1990  Tsukamoto et al. .................. 546/16

FOREIGN PATENT DOCUMENTS 0239309  3/1987  European Pat. Off. ............. 546/16
0291673  3/1988  European Pat. Off. ............ 546/329
0311313  9/1988  European Pat. Off. .

OTHER PUBLICATIONS

Takemura et al., Chem. Pharm. Bull. 29, 10, 3019–3025 (1981), "Synthesis and Selective Activity of Cholinergic Agents with Rigid Skeletons".
Coldham et al., Tet. Letters, 29, 41, 5321 (1988), "Stereochemically Controlled Synthesis of Spirocyclic Lactones and Ethers from N-Methyl-4-Piperidone and 3-Quinuclidinone by Phenylthio Migration".
Shapiro et al., Chem. Ab., vol. 90, 602, (1979), "Synthesis of Nitroxyl Radicals Based on 4-Ethynyl-4-Hydroxy-2,2,6,6-Tetramethylpiperidine", (90:203838k).
Azerbaev et al., Hetero. Compounds, vol. 74, 111885 (1971), "Synthesis of 1,2,5-Trimethyl-4-(3-Hydroxy-1-Propynyl)-4-Piperidinol and Its Reactions", (111879r).
Azerbaev et al., Hetero. Compounds, vol. 70, 96659 (1969), "Synthesis and Reactions of 2,5-Dimethyl-4-(-3-Methyl-3-Hydroxy-1-Butynyl)-4-Piperidinol", (96659r).

Primary Examiner—Robert T. Bond
Attorney, Agent, or Firm—Marshall, O'Toole, Gerstein, Murray & Bicknell

[57] ABSTRACT

Compounds of general formula I,

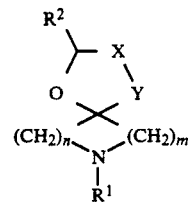

wherein
  $R^1$ represents hydrogen or alkyl $C_{1-3}$,
  $R^2$ represents hydrogen or alkyl $C_{1-6}$,
  n and m are integers from 1 to 3, provided that n+m=4, and
  one of X and Y represents $CH_2$ and the other represents $CHR^3$, C=O, C=$CHR^4$ or C=$NR^5$, in which
  $R^3$, $R^4$ and $R^5$ are as defined in the specification,
  and their salts
  are useful as pharmaceuticals, in particular as central muscarinic acetylcholine receptors. The compounds are therefore useful in the treatment of diseases such as presenile and senile dementia, Huntington's chorea, tardive dyskinesia, hyperkinesia, mania and Tourette Syndrome, and also as analgesic agents for use in the treatment of severe painful conditions such as rheumatism, arthritis, and terminal illness.

3 Claims, No Drawings

SPIROFURANE DERIVATIVES

This invention relates to novel chemical compounds, processes for their preparation, pharmaceutical compositions containing them, and methods of treatment involving their use.

According to the invention there are provided compounds of formula I,

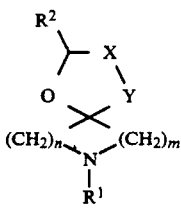

wherein
$R^1$ represents hydrogen or alkyl $C_{1-3}$,
$R^2$ represents hydrogen or alkyl $C_{1-6}$,
n and m are integers from 1 to 3, provided that $n+m=4$, and
one of X and Y represents $CH_2$ and the other represents $CHR^3$, $C=O$, $C=CHR^4$ or $C=NR^5$, in which
$R^3$ represents OH, alkoxy $C_{1-6}$, alkanoyloxy $C_{1-6}$, $NR^2R^2$, $CO_2R^2$, 3-methyl-1,2,4-oxadiazol-5-yl, or 3-amino-1,2,4-oxadiazol-5-yl,
$R^4$ represents hydrogen, alkyl $C_{1-6}$, alkanoyl $C_{1-6}$ or $COOR^2$, and
$R^5$ represents OH, alkoxy $C_{1-6}$ or alkanoyloxy $C_{1-6}$.

Also included within the scope of the present invention are salts of the compounds of formula I. It will be appreciated that salts of the compounds for use in medicine will be non-toxic pharmaceutically acceptable salts. Other salts may, however, be useful, in the preparation of the compounds of formula I or their non-toxic pharmaceutically acceptable salts. Acid addition salts, for example, may be formed by mixing a solution of the compound of formula I with a solution of a pharmaceutically acceptable non-toxic acid such as hydrochloric acid, fumaric acid, maleic acid, succinic acid, carbonic acid or phosphoric acid.

Preferred compounds of formula I are those in which Y represents $CH_2$, and those in which n and m both represent 2.

Alkyl groups which $R^2$ may represent include methyl, ethyl, n-propyl, iso-propyl, n-butyl, iso-butyl, s-butyl and t-butyl. We prefer compounds, however, in which $R^2$ represents hydrogen or methyl.

Alkyl groups which $R^1$ may represent include methyl, ethyl, n-propyl and iso-propyl. We particularly prefer compounds in which $R^1$ represents methyl.

Alkoxy groups which $R^3$ may represent include in particular methoxy and ethoxy. Alkanoyloxy groups which $R^3$ may represent include in particular acetoxy.

As a particularly preferred sub-group of compounds there are provided compounds of formula I, in which
$R^2$ represents methyl,
n and m both represent 2,
Y represents $CH_2$, and
$R^1$ and X are as defined above.

Preferred compounds are those in which X represents $C=O$.

Many of the compounds of the present invention have at least one asymmetric centre and can therefore exist as enantiomers, and in some cases as diastereomers.

It is to be understood that the invention covers all such isomers and mixtures thereof.

The compounds of the present invention are useful because they possess pharmacological activity in animals. In particular, the compounds stimulate central muscarinic acetylcholine receptors as can be demonstrated in studies of the affinity constants of the compounds for [$^3$H]-oxotremorine-M binding sites in rat cortical membrane preparations. The compounds may therefore be useful in the treatment of neurological and mental illnesses whose clinical manifestations are due to involvement of specific populations of cholinergic neurones. Such diseases include presenile and senile dementia (also known as Alzheimer's disease and senile dementia of the Alzheimer type respectively), Huntington's chorea, tardive dyskinesia, hyperkinesia, mania and Tourette Syndrome. The compounds are also useful analgesic agents and therefore useful in the treatment of severe painful conditions such as rheumatism, arthritis, and terminal illness.

Thus, according to another aspect of the invention, there is provided a method of treatment of a condition selected from the group consisting of presenile and senile dementia, Huntington's chorea, tardive dyskinesia, hyperkinesia, mania and Tourette Syndrome, which method comprises administering to a patient suffering from that condition a therapeutically effective quantity of one or more compounds of formula I.

The compounds of the invention may be administered by any convenient route, e.g. orally, parenterally or rectally. The daily dose required will of course vary with the particular compound used, the particular condition being treated and with the severity of that condition. However, in general a total daily dose of from about 0.1 to 10 mg/kg of body weight, preferably about 0.1 to 1 mg/kg is suitable, administered from 1 to 4 times a day.

For use in the method of treatment of the invention the compound of formula I will generally be administered in the form of a suitable pharmaceutical composition. Thus, according to another aspect of the invention, there is provided a pharmaceutical composition comprising a compound of formula I in admixture with a pharmaceutically acceptable carrier.

The pharmaceutical composition is preferably in unit dose form. Such forms include solid dosage forms, e.g. tablets, pills, capsules, powders, granules, and suppositories for oral, parenteral or rectal administration, and liquid dosage forms, e.g. sterile parenteral solutions or suspensions, suitably flavoured syrups, flavoured emulsions with edible oils such as cottonseed oil, sesame oil, coconut oil and peanut oil, and elixirs and similar pharmaceutical vehicles.

Solid compositions may be prepared by mixing the active ingredient with pharmaceutical carriers, e.g. conventional tabletting ingredients such as corn starch, lactose, sucrose, sorbitol, talc, stearic acid, magnesium stearate, dicalcium phosphate, gums and other diluents, e.g. water, to form a homogeneous preformulation composition in which the active ingredient is uniformly dispersed so that it may be readily subdivided into equally effective unit dosage forms containing typically from 0.1 to about 500 mg of the active ingredient. The solid dosage forms may be coated or otherwise compounded to prolong the action of the composition.

In order to reduce unwanted peripherally mediated side effects, it may be advantageous to include in the composition a peripherally acting cholinergic antagonist (or anti-muscarinic agent) such as N-methylscopolamine, N-methylatropine propantheline, methantheline or glycopyrrolate.

The compounds of formula I may be prepared by various routes. For example, compounds of formula I may be prepared by cyclisation of a compound of formula II,

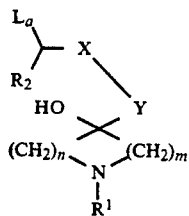

in which $L_a$ represents a leaving group such as, for example, halogen, e.g. bromo, or hydroxy. Procedures which may be used are analogous to those described by Picard, P and Mouliner, J (*Bull Soc Chim.* Z889, (1974)). Specific details are given in the Examples below.

In addition, certain compounds of formula I may be prepared by appropriate modification of other compounds of formula I. For example, compounds of formula I in which X or Y represents C=O may be prepared by oxidation of the corresponding compound in which X or Y represents CHOH. The oxidation may be performed by conventional techniques, e.g. using oxalyl chloride in an inert solvent at reduced temperatures, e.g. $-50°$ to $-100°$ C. Conversely, compounds of formula I in which X or Y represents CHOH may be prepared by reduction of corresponding compounds in which X or Y represents C=O.

Compounds of formula I in which X or Y represents $CHR^3$ in which $R^3$ is alkoxy or alkanoyloxy may be prepared from the corresponding compounds in which $R^3$ is hydroxyl by conventional techniques.

Compounds of formula I in which X or Y represents $C=NR^5$ may be prepared by reaction of the corresponding compound in which X or Y represents C=O with a nitrogen nucleophile of formula $H_2NR^5$. The reaction may be carried out by mixing the carbonyl compound and the nitrogen compound at room temperature.

Compounds of formula I in which X or Y represents $CHR^3$ in which $R^3$ is a primary amine, a monoalkylamine or a dialkylamine may be prepared by the reduction of the corresponding imines (i.e. compounds in which X or Y represents $C=NR^6$ wherein $R^6$ is hydroxyl or alkyl $C_{1-6}$), or an immonium salt (X or Y represents $C=N^+(R^7R^8)$ wherein $R^7$ and $R^8$ are alkyl $C_{1-6}$). The imines and immonium salts may be prepared from the ketones by conventional methods.

Compounds of formula I in which X or Y represents CH-COOH may be prepared by reaction of the corresponding compound in which X or Y represents C=O with the lithium salt of 2-(trimethylsilyl)-1,3-dithiane followed by hydrolysis. The corresponding esters and oxadiazole derivatives may be prepared from the dithiane derivatives according to the methods of Saunders et al (*J Chem Soc Chem Commun* 1618–1619 (1988)).

Compounds of formula I in which X or Y represents $C=CHR^4$ may be prepared by conventional Wittig condensations of the corresponding compounds in which X or Y represents C=O with a Wittig reagent, for example a compound of the formula $R^4CH=P(Ph)_3$.

In any of the above reactions it may be necessary and/or desirable to protect any sensitive groups in the compounds. For example, $R^1$ may be replaced by a suitable amine protecting group such as benzyloxycarbonyl, t-butyloxycarbonyl or ethoxycarbonyl. The protecting groups may be removed at any convenient stage in the synthesis of the desired compound by conventional methods.

The invention will now be illustrated, but in no way limited, by the following Examples in which all temperatures are in degrees Celsius, THF is tetrahydrofuran, DMSO is dimethyl sulphoxide and ether is diethylether.

EXAMPLE 1

8-Methyl-3-methylene-1-oxa-8-azaspiro[4.5]decane maleate a)

1-Ethoxycarbonyl-4-hydroxy-4-[2-(dimethylaminomethyl)-2-propenyl]piperidine

2-[(Dimethylamino)methyl]propene (29.75 g, 300 mmol) in anhydrous THF (300 ml) was cooled to $-78°$ and butyl lithium (2.5M, 120 ml, 300 mmol) was added dropwise, the temperature of addition being maintained below 0°. The dry-ice bath was replaced by an ice-bath and the reaction mixture maintained at 0° for 3 hours and then cooled to $-78°$. 1-Ethoxycarbonyl-4-piperidinone (25.68 g, 150 mmol) in anhydrous THF (50 ml) was added dropwise and the reaction mixture maintained at $-78°$ for 1.5 hours and then stirred at room temperature overnight. Approximately 50 g of ice was added and the reaction mixture washed with saturated NaCl several times and dried (MgSO$_4$), yielding a tan, viscous oil (42.47 g). Purification by flash chromatography eluting with ethylacetate in hexane gave the sub-title compound (9.33 g)

b)

1-Ethoxycarbonyl-4-hydroxy-4-[2-(bromomethyl)-2-propenyl] piperidine

Solid CNBr (1.39 g, 13.16 mmol) was added to a solution of the product of step a) (3.04 g, 11.24 mmol) in dichloromethane (55 ml) at 0° and stoppered. The reaction mixture was stirred at 0° for 2.5 hours. Evaporation and purification on a silica gel, eluting with MeOH/CH$_2$Cl$_2$ gave the sub-title compound (1.5 g).

c) 8-Ethoxycarbonyl-3-methylene-1-oxa-8-azaspiro[4.5] decane

The product of step b) (1.50 g, 0.0066 mmol), 50% NaOH (15 ml) and THF (20 ml) were mixed and stirred overnight. The reaction mixture was diluted with CH$_2$Cl$_2$/H$_2$O and separated. The aqueous layer was further extracted with CH$_2$Cl$_2$ (50 ml×2) and worked-up to give 1.42 g of a tan oil.

d) 8-Methyl-3-methylene-1-oxa-8-azaspiro[4.51]decane

Vitride (NaAlH$_2$(OCH$_2$CH$_2$OCH$_3$)$_2$, 70%, 4.48 g, 15.5 mmol) was dissolved in toluene (approximately 10 ml) and added to a solution of the product of step c) (1.1 g, 5 mmol) in toluene (10 ml). The reaction mixture was cooled in an ice-bath, maintained at room temperature for 1 hour and then cooled to 0° C. 4.48 ml of H$_2$O followed by 15% NaOH (4.48 ml) and water (13.44 ml) was added carefully. A milky suspension was formed.

The toluene layer was separated and the aqueous layer extracted with toluene (15 ml×2). Work-up gave the title compound as a tan oil (0.68 g). The free base crystallised on standing and the colour changed from tan to brown.

e) 8-Methyl-3-methylene-1-oxa-8-azaspiro[4.5]decane maleate

The product of step d) (1.68 g, 10 mmol) was dissolved in a small amount of ispropyl alcohol and mixed with a solution of maleic acid (1.20 g, 10.3 mmol) in isopropyl alcohol. Evaporation and recrystallisation of the residue from ethyl acetate and ether gave white prisms (1 g), mp 95-97.

|          | C     | H    | N    |
|----------|-------|------|------|
| Theory:  | 59.35 | 7.47 | 4.94 |
| Found:   | 59.30 | 7.45 | 4.95 |

EXAMPLE 2

3-Hydroxy-8-methyl-1-oxa-8-azaspiro[4.5]decane hydrochloride a) 1-Ethoxycarbonyl-4-hydroxy-4-(2-propenyl)-piperidine

Allyl magnesium bromide was prepared in situ by suspending Mg turnings (21.2 g, 0.87 mol) in dry ether (700 ml) and adding allyl bromide (34.8 g, 0.29 mol) gradually until the reaction initiated and then at sufficient rate to maintain reflux. The reaction was stirred at room temperature for 1.5 hours.

The reaction was cooled to −15° with a methanol/ice bath and acetone (25 g, 0.146 mol) was added in ether (700 ml) The reaction was stirred at room temperature for four hours and then left overnight.

The reaction was cooled with an ice bath while quenching with ammonium chloride (360 ml of a saturated solution diluted to 1440 ml). The reaction was stirred and the phases separated. The aqueous layer was extracted once more with ether and the combined organic layers were washed with brine, dried and stripped. Purification by flash chromatography on silica and elution with $CHCl_3/NH_3$, then $MeOH/CHCl_3/NH_3$ gave the sub-title compound as a yellow oil (17.2 g).

b) 1-Ethoxycarbonyl-4-hydroxy-4-(2,3-epoxypropyl)-piperidine

The product of step a) (17.2 g, 0.081 mol) was dissolved in dry $CH_2Cl_2$ (370 ml) under nitrogen. m-Chloroperbenzoic acid (80%, 35 g, 0.16 mol) was added and the reaction was stirred at room temperature overnight. The white precipitate was removed by suction filtration, and washed with $CH_2Cl_2$. The $CH_2Cl_2$ was washed with 10% sodium sulphite and this was extracted once with $CH_2Cl_2$. The combined organic layers were washed with 10% sodium hydrogen carbonate and this was extracted with $CH_2Cl_2$. The combined organic layers were dried over $Na_2SO_4$ and stripped. The yellow oil obtained was stored under nitrogen in the freezer. Purification by silica flash chromatography, eluting with $MeOH/CHCl_3$ gave the sub-title compound as a yellow oil (11.1 g).

c) 1-Ethoxycarbonyl-4-hydroxy-4-(2,3-dihydroxypropyl)-piperidine

The partially purified product of step b) (78.9 g, 0.34 mol) was dissolved in 250 ml of THF and 500 ml of deionized water. Concentrated $HClO_4$ (50 ml) was added and the reaction was stirred overnight. The solution was cooled with an ice bath and neutralized with saturated aqueous $NaHCO_3$. The suspension was then washed with $CH_2Cl_2$, and this was back-extracted with $H_2O$.

The aqueous layers were stripped. The resulting residue was digested with four portions of methanol. These were combined, diluted with $CHCl_3$, and dried over $Na_2SO_4$. The solvents were stripped and the crude was purified by eluting from silica with an ammoniated methanol/$CHCl_3$ gradient. This gave 37.3 g of brown oil or 13% for the three steps from the ketone.

d) 8-Ethoxycarbonyl-3-hydroxy-1-oxa-8-azaspiro[4.5]decane

The product of step c) (5.2 g, 0.021 mol) was dissolved in dry pyridine (60 ml), placed under nitrogen and cooled with an ice-bath. Tosyl chloride (4.8 g, 0.025 mol) was dissolved in pyridine (30 ml) and added dropwise. The reaction was heated at 110°. After 5 hours another 2.2 g (0.011 mol) tosyl chloride was added in 20 ml pyridine at room temperature and the heating was continued overnight.

The pyridine was removed as an azeotrope with three portions of toluene and the residue digested seven times with anhydrous ether. The combined organic extracts were filtered and stripped. Purification on silica, flash column using $MeOH/CHCl_3/NH_3$ gave the sub-title compound as a colourless oil (1.1 g). Further ether digestion of the residue, followed by extraction with ether and purification gave a further 1.3 g of product.

e) 3-Hydroxy-8-methyl-1-oxa-8-azaspiro[4.5]decane hydrochloride

The product of step d) (1.3 g, 5.7 mmol) was dissolved in dry THF (60 ml), placed under nitrogen and cooled with an ice bath. Vitride (70%, 2.7 ml) in THF (30 ml) was added dropwise and the reaction stirred at room temperature overnight. Three further portions of Vitride (5 ml each) in THF (15 ml each) were added dropwise to the cooled solution and after each portion the solution was stirred for several hours. The reaction was cooled again and treated with 5% NaOH until evolution of hydrogen cease.

The addition of NaOH was continued at room temperature until a sticky white paste had precipitated. The THF was decanted, suction filtered, and the paste washed once with THF. The solvent was then dried and stripped, and the paste washed once with THF. Purification by silica flash column using $MeOH/CHCl_3$ gave a viscous yellow oil (1.1 g) which partially solidified on standing to white needles. The solid was taken up in isopropyl alcohol and the solution cooled and acidified with HCl/ethanol. This gave a white precipitate which was collected and washed with cold ether to yield the title compound as the hydrochloride salt (0.47 g), mp 228-229°.

EXAMPLE 3

8-Methyl-1-oxa-8-azaspiro[4.5]decan-3-one

Oxalyl chloride (1.9 g, 14.3 mmol) was dissolved in dry $CH_2Cl_2$ (150 ml), placed under $N_2$ and cooled to −60° with a dry ice/acetone bath. Dry DMSO (2.2 g, 29 mmol) in dry $CH_2Cl_2$ (30 ml) was added in slow drops. The reaction was stirred for 10 minutes. The free base of Example 2 (1.5 g, 8.8 mmol) in $CH_2Cl_2$ (100 ml) was added in slow drops, the temperature being maintained below −60°. The reaction was stirred for 20 minutes and then was treated dropwise with diisopropylethylamine (9.0 g, 67.5 mmol).

The bath was removed and the reaction allowed to warm somewhat. The solution was treated with distilled water (150 ml) in rapid drops. The layers were separated and the aqueous layer was extracted three times with $CH_2Cl_2$. A little saturated $Na_2CO_3$ was added and two more $CH_2Cl_2$ extractions were done.

The organic layers were dried with $Na_2SO_4$ and stripped. Purification by silica flash chromatography, using $MeOH/CHCl_3/NH_3$ gave the title product as a yellow oil (1.5 g).

EXAMPLE 3A

8-Methyl-1-oxa-8-azaspiro[4.5]decan-3-one maleate

The yellow oil obtained in Example 3 was taken up in ethyl acetate, the solution cooled in an ice bath and maleic acid/ethyl acetate was added. The title compound was obtained as an off-white powder, mp 127–128.5°.

|         | C     | H    | N    |
|---------|-------|------|------|
| Theory: | 54.73 | 6.71 | 4.91 |
| Found:  | 54.33 | 6.55 | 4.77 |

NMR (DMSO): δ6.1(2H), 4.0(2H), 3.3(4H,m), 2.8(3H), 2.0(4H,m)
IR (KBr): 2675, 1760, 1580, 1360, 1380, 930 cm$^{-1}$
$(M+1)+=170$

EXAMPLE 4

8-Methyl-1-oxa-8-azaspiro[4.5]decan-3-one oxime

The compound of Example 3 (0.6 g, 3.5 mmol) was dissolved in methanol (50 ml) and placed under nitrogen. Hydroxylamine hydrochloride was added and the reaction was stirred at room temperature overnight.

The solvent was evaporated, and the residue taken up in $CHCl_3$ and treated with saturated $Na_2CO_3$. The layers were separated and the basic layer extracted with three more portions of $CHCl_3$. The combined organic extracts were dried with $Na_2SO_4$ and stripped. Purification by silica flash chromatography using $MeOH/CHCl_3/NH_3$ gave the title compound as a pale yellow solid.

EXAMPLE 4A

8-Methyl-1-oxa-8-azaspiro[4.5]decan-3-one oxime maleate

The compound of Example 4 (0.76 g, 4.1 mmol) was dissolved in hot ethyl acetate and mixed with maleic acid (0.48 g, 0.41 mmol) to give the title compound as a white solid, mp 183–184°.

|         | C     | H    | N    |
|---------|-------|------|------|
| Theory: | 51.99 | 6.71 | 9.33 |
| Found:  | 51.79 | 6.63 | 9.20 |

NMR (DMSO): δ 6.1(2H), 4.4(2H), 3.1(4H,m), 2.8(3H), 1.9(4H)
IR (KBr): 3250, 2700, 2450, 1580, 1360, 1380 cm$^{-1}$
$(M+1)+=185$

EXAMPLE 5

3-Acetoxy-8-methyl-1-oxa-8-azaspiro[4.5]decane fumarate

3-Hydroxy-8-methyl-1-oxa-8-azaspiro[4.5]decane (0.9 g, 5.3 mmol) was combined with acetic anhydride (3 ml) and heated under nitrogen at 80° for 1 hour. The cooled reaction mixture was poured into water and basified with saturated sodium carbonate solution. The aqueous mixture was extracted with chloroform, backwashed with brine and dried over $Na_2SO_4$. The solvent was evaporated to give an oil (0.68 g) which was dissolved in ether and treated with approximately 1 equivalent of fumaric acid in ether. A sticky solid precipitated immediately. On standing a white solid formed which was filtered, washed with ether and dried at 45° to give the ester as the fumarate salt, mp 122–123° (dec).

|         | C     | H    | N    |
|---------|-------|------|------|
| Theory: | 54.70 | 7.04 | 4.25 |
| Found:  | 54.48 | 7.05 | 4.18 |

EXAMPLE 6

8-Methyl-1-oxa-8-azaspiro[4.5]decan-3-one oxime methyl ether

The ketone of example 3 (0.5 g, 3 mmol) was dissolved in methanol (30 ml) under a nitrogen atmosphere. Methoxyamine hydrochloride (0.25 g) was added and the solution was stirred at room temperature for 2 hours. Another 0.02 g of reagent was added and stirring was continued for 3 days. The methanol was evaporated and the residue was dissolved in chloroform and washed with saturated aqueous sodium carbonate. The chloroform layer was dried over $Na_2SO_4$ and evaporated to give a crude product which was purified by flash chromatography over silica gel and eluted with ammoniated 5% and 10% methanol/chloroform. Concentration of the solvent afforded a residue which was dissolved in ether and treated with fumaric acid dissolved in ether while warming on a steam bath. The precipitated solid was kept at room temperature overnight then it was collected by filtration and washed with ether to give 0.35 g of the fumarate salt, mp 149–152°.

|         | C     | H    | N    |
|---------|-------|------|------|
| Theory: | 53.49 | 7.05 | 8.91 |
| Found:  | 53.22 | 7.00 | 8.77 |

EXAMPLE 7

3-Methoxy-8-methyl-1-oxa-8-azaspiro[4.5]decane a)
8-Ethoxycarbonyl-3-methoxy-1-oxa-8-azaspiro[4.5]decane 8-Ethoxycarbonyl-3-hydroxy-1-oxa-8-azaspiro[4.5]-decane (1 g, 0.0044 mol) was dissolved in anhydrous THF (40 ml) under nitrogen and cooled with an ice-bath. Sodium hydride (0.22 g, 5.5 mmol as a 60% oil dispersion) was added and the reaction was stirred at 0° C. for 20 minutes. Methyl iodide (2.0 g, 0.9 ml) in THF (10 ml) was added dropwise. The reaction was allowed to warm to room temperature and stirred for 3 hours. An additional 0.9 ml of methyl iodide was added at 0° C. and stirring was continued overnight. The cooled reaction was diluted with water (10 ml). The aqueous THF was washed with saturated brine and dried over $Na_2SO_4$. The solvents were evaporated and the residue was purified by flash chromatography on silica gel by elution with ammoniated 2% methanol/chloroform. Evaporation of the solvents gave 0.97 g of a pale orange oil.

b) 3-Methoxy-8-methyl-1-oxa-8-azaspiro[4.5]decane

A solution of the carbamate prepared as in step (a) (1.4 g, 60 mmol) in THF (60 ml) under nitrogen was cooled with an ice-bath and reduced with Vitride (70% solution, 6.6 ml or 240 mmol) in dry THF (75 ml) according to the method of example 2(e) to give the title compound as a pale yellow oil (0.76 g).

EXAMPLE 8

3-Hydroxy-2,8-dimethyl-1-oxa-8-azaspiro[4.5]deoane a)
4-(3-Hydroxy-1-butynyl)-1-ethoxycarbonyl-4-piperidinol A solution of 3-butyn-2-ol (42 g, 0.6 mol) in dry THF (8OO ml) under nitrogen was cooled with a dry-ice/acetone bath. n-Butyl lithium (390 ml of 2.5M and 230 ml of 1.5M) in hexane was added rapidly, dropwise. The suspension became gelatinous and another 800 mls of dry THF was added. The reaction was stirred at approximately −78° for 1 hour and then at 0° for 20 minutes. The reaction was cooled to −78° and 1-ethoxycarbonyl-4-piperidinone (104 g, 0.607 mol) in 300 ml of dry THF was added rapidly dropwise. The reaction mixture was allowed to warm to room temperature and then stirred overnight. The reaction mixture was cooled in an ice-bath, diluted with THF (1.51), decomposed with saturated $NH_4Cl$, and the THF layer was washed three times with 200 ml of saturated ammonium chloride. The aqueous layers were back-washed with THF (200 ml×3). The organic layers were combined and dried over $MgSO_4$ and evaporated to give an oil. A one-fifth portion of the oil was purified by flash chromatography on silica gel and elution with 30% ethyl acetate/ether afforded the desired product diol (19.7 g).

b)
8-Ethoxycarbonyl-2-methyl-1-oxa-8-azaspirodecan-3-one

The diol of step a) (19.7 g, 0.082 mol) was dissolved in ethanol (82 ml) and water (7.4 g, 0.41 mol). Mercury/Nafion NR50 (41 g) prepared according to Y Saimoto et al (Bull Chem Soc Japan, 56, 3078 (1983)) was added and the slurry was stirred in a closed flask for three days. The resin was filtered off and washed with methylene chloride. The combined filtrates were evaporated. The residue was dissolved as far as possible in ether and filtered through a bed of silica gel to clarify the solution. The filtrate was evaporated to give the ketone as a yellow oil (13.3 g).

c) 3-Hydroxy-2,8-dimethyl-1-oxa-8-azaspiro[4.5]decane

The ketone from step b) (10.2 g, 0.042 mol) was dissolved in dry THF (375 ml) under nitrogen and cooled in an ice-bath. Vitride (57 ml, 0.021 mol), diluted with THF (450 ml) was added dropwise and the reaction was stirred at room temperature overnight. The reaction was decomposed with water according to the method of example 2(e) and the desired title compound was isolated as an oil.

EXAMPLE 9

2,8-Dimethyl-1-oxa-8-azaspiro[4.5]decan-3-one

The alcohol from Example 8 is oxidised according to the procedure described in Example 3 above to give the ketone.

EXAMPLE 9A 2,8-Dimethyl-1-oxa-8-azaspiro[4.5]decan-3-one fumarate mp 139–141°.

We claim:

1. A compound selected from the group consisting of 2,8-dimethyl-1-oxa-8-azaspiro[4.5]decan-3-one and salts thereof.

2. A method of treatment of a condition selected from the group consisting of presenile and senile dementia, Huntington's chorea, tardive dyskinesia, hyperkinesia, mania, and Tourette Syndrome, which method comprises administering to a patient suffering from such condition, a therapeutically-effective quantity of a compound in accordance with claim 1.

3. A pharmaceutical composition for treatment of neurological and mental illnesses comprising an effective amount of a compound in accordance with claim 1 in admixture with a pharmaceutically-acceptable carrier.

* * * * *